(12) United States Patent
Govea

(10) Patent No.: US 9,089,689 B2
(45) Date of Patent: Jul. 28, 2015

(54) METHODS OF MAKING SEGMENTED ELECTRODE LEADS USING FLANGED CARRIER

(71) Applicant: BOSTON SCIENTIFIC NEUROMODULATION CORPORATION, Valencia, CA (US)

(72) Inventor: Michael X. Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/469,214

(22) Filed: Aug. 26, 2014

(65) Prior Publication Data

US 2015/0066120 A1     Mar. 5, 2015

Related U.S. Application Data

(60) Provisional application No. 61/872,465, filed on Aug. 30, 2013.

(51) Int. Cl.
*A61N 1/05*     (2006.01)

(52) U.S. Cl.
CPC ............... *A61N 1/0534* (2013.01); *A61N 1/05* (2013.01)

(58) Field of Classification Search
None
See application file for complete search history.

(56) References Cited

U.S. PATENT DOCUMENTS

| 4,602,624 A | 7/1986 | Naples et al. |
| 4,630,611 A | 12/1986 | King |
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |

(Continued)

FOREIGN PATENT DOCUMENTS

| EP | 0580928 A1 | 2/1994 |
| EP | 0650694 B1 | 7/1998 |

(Continued)

OTHER PUBLICATIONS

U.S. Appl. No. 14/557,211, filed Dec. 1, 2014.

(Continued)

*Primary Examiner* — Brian T Gedeon
(74) *Attorney, Agent, or Firm* — Lowe Graham Jones PLLC; Bruce E. Black

(57) ABSTRACT

A method of making a stimulation lead includes providing a carrier with a body having a first surface, a distal end, and a proximal end. The carrier also includes flanges and each flange has a leg portion attached to the body and extending away from the first surface at a non-zero angle. The method further includes attaching segmented electrodes to the first surface of the carrier; attaching conductors to the segmented electrodes; forming the carrier into a cylinder with the cylinder defining a central longitudinal axis through a center of the cylinder with the segmented electrodes disposed within the cylinder and the leg portions of the flanges extending toward the central longitudinal axis of the cylinder; molding a lead body around the segmented electrodes disposed on the carrier and around the flanges; and removing at least a portion of the carrier to separate the segmented electrodes.

20 Claims, 9 Drawing Sheets

(56) References Cited

U.S. PATENT DOCUMENTS

| | | | |
|---|---|---|---|
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |
| 6,181,969 B1 | 1/2001 | Gord | |
| 6,322,559 B1 | 11/2001 | Daulton et al. | |
| 6,510,347 B2 | 1/2003 | Borkan | |
| 6,516,227 B1 | 2/2003 | Meadows et al. | |
| 6,556,873 B1 | 4/2003 | Smits | |
| 6,564,078 B1 | 5/2003 | Marino et al. | |
| 6,609,029 B1 | 8/2003 | Mann et al. | |
| 6,609,032 B1 | 8/2003 | Woods et al. | |
| 6,678,564 B2 | 1/2004 | Ketterl et al. | |
| 6,741,892 B1 | 5/2004 | Meadows et al. | |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,244,150 B1 | 7/2007 | Brase et al. | |
| 7,292,890 B2 | 11/2007 | Whitehurst et al. | |
| 7,450,997 B1 | 11/2008 | Pianca et al. | |
| 7,489,971 B1 | 2/2009 | Franz | |
| 7,668,601 B2 | 2/2010 | Hegland et al. | |
| 7,672,734 B2 | 3/2010 | Anderson et al. | |
| 7,761,165 B1 | 7/2010 | He et al. | |
| 7,761,985 B2 | 7/2010 | Hegland et al. | |
| 7,765,011 B2 * | 7/2010 | Skubitz et al. | 607/115 |
| 7,783,359 B2 | 8/2010 | Meadows | |
| 7,792,590 B1 | 9/2010 | Pianca et al. | |
| 7,809,446 B2 | 10/2010 | Meadows | |
| 7,840,188 B2 | 11/2010 | Kurokawa | |
| 7,848,802 B2 | 12/2010 | Goetz | |
| 7,856,707 B2 | 12/2010 | Cole | |
| 7,860,570 B2 | 12/2010 | Whitehurst et al. | |
| 7,949,395 B2 | 5/2011 | Kuzma | |
| 7,974,705 B2 | 7/2011 | Zdeblick et al. | |
| 7,974,706 B2 | 7/2011 | Moffitt et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,099,177 B2 | 1/2012 | Dahlberg | |
| 8,175,710 B2 | 5/2012 | He | |
| 8,224,450 B2 | 7/2012 | Brase | |
| 8,225,504 B2 | 7/2012 | Dye et al. | |
| 8,271,094 B1 | 9/2012 | Moffitt et al. | |
| 8,295,944 B2 | 10/2012 | Howard et al. | |
| 8,321,025 B2 | 11/2012 | Bedenbaugh | |
| 8,359,107 B2 | 1/2013 | Pianca et al. | |
| 8,364,278 B2 | 1/2013 | Pianca et al. | |
| 8,391,985 B2 | 3/2013 | McDonald | |
| 2,583,237 A1 | 11/2013 | Bedenbaugh | |
| 8,688,235 B1 | 4/2014 | Pianca et al. | |
| 8,868,206 B2 * | 10/2014 | Barker et al. | 607/116 |
| 8,897,889 B2 * | 11/2014 | Pianca et al. | 607/116 |
| 2002/0156513 A1 | 10/2002 | Borkan | |
| 2002/0183817 A1 | 12/2002 | Van Venrooij et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0247697 A1 | 11/2006 | Sharma et al. | |
| 2007/0150036 A1 | 6/2007 | Anderson | |
| 2007/0203546 A1 | 8/2007 | Stone et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2008/0255647 A1 * | 10/2008 | Jensen et al. | 607/119 |
| 2009/0187222 A1 | 7/2009 | Barker | |
| 2009/0204192 A1 | 8/2009 | Carlton et al. | |
| 2009/0276021 A1 | 11/2009 | Meadows et al. | |
| 2010/0030298 A1 | 2/2010 | Martens et al. | |
| 2010/0036468 A1 | 2/2010 | Decre et al. | |
| 2010/0076535 A1 | 3/2010 | Pianca et al. | |
| 2010/0082076 A1 | 4/2010 | Lee et al. | |
| 2010/0094387 A1 | 4/2010 | Pianca et al. | |
| 2010/0268298 A1 | 10/2010 | Moffitt et al. | |
| 2010/0269338 A1 | 10/2010 | Dye | |
| 2010/0269339 A1 | 10/2010 | Dye et al. | |
| 2010/0287770 A1 | 11/2010 | Dadd et al. | |
| 2011/0004267 A1 | 1/2011 | Meadows | |
| 2011/0005069 A1 | 1/2011 | Pianca | |
| 2011/0047795 A1 | 3/2011 | Turner et al. | |
| 2011/0056076 A1 | 3/2011 | Hegland et al. | |
| 2011/0077699 A1 | 3/2011 | Swanson et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0131808 A1 | 6/2011 | Gill | |
| 2011/0238129 A1 | 9/2011 | Moffitt et al. | |
| 2011/0245903 A1 | 10/2011 | Schulte et al. | |
| 2011/0301665 A1 | 12/2011 | Mercanzini et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2012/0316615 A1 | 12/2012 | DiGiore et al. | |
| 2013/0105071 A1 | 5/2013 | DiGiore et al. | |
| 2013/0109254 A1 | 5/2013 | Klardie et al. | |
| 2013/0197424 A1 | 8/2013 | Bedenbaugh | |
| 2013/0197602 A1 | 8/2013 | Pianca et al. | |
| 2013/0261684 A1 | 10/2013 | Howard | |
| 2013/0317587 A1 | 11/2013 | Barker | |
| 2013/0325091 A1 | 12/2013 | Pianca et al. | |
| 2014/0039587 A1 | 2/2014 | Romero | |
| 2014/0142671 A1 | 5/2014 | Moffitt et al. | |
| 2014/0180375 A1 | 6/2014 | Pianca et al. | |
| 2015/0000124 A1 * | 1/2015 | Barker et al. | 29/825 |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0047272 | 8/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 14/286,889, filed May 23, 2014.
U.S. Appl. No. 14/286,934, filed May 23, 2014.
U.S. Appl. No. 14/286,829, filed May 23, 2014.
U.S. Appl. No. 14/286,940, filed May 23, 2014.
U.S. Appl. No. 14/332,212, filed Jul. 15, 2014.
U.S. Appl. No. 14/452,461, filed Aug. 5, 2014.
U.S. Appl. No. 14/286,797, filed May 23, 2014.
U.S. Appl. No. 14/325,249, filed Jul. 7, 2014.
International Search Report and Written Opinion for PCT/US2014/052729 mailed Nov. 11, 2014.

* cited by examiner

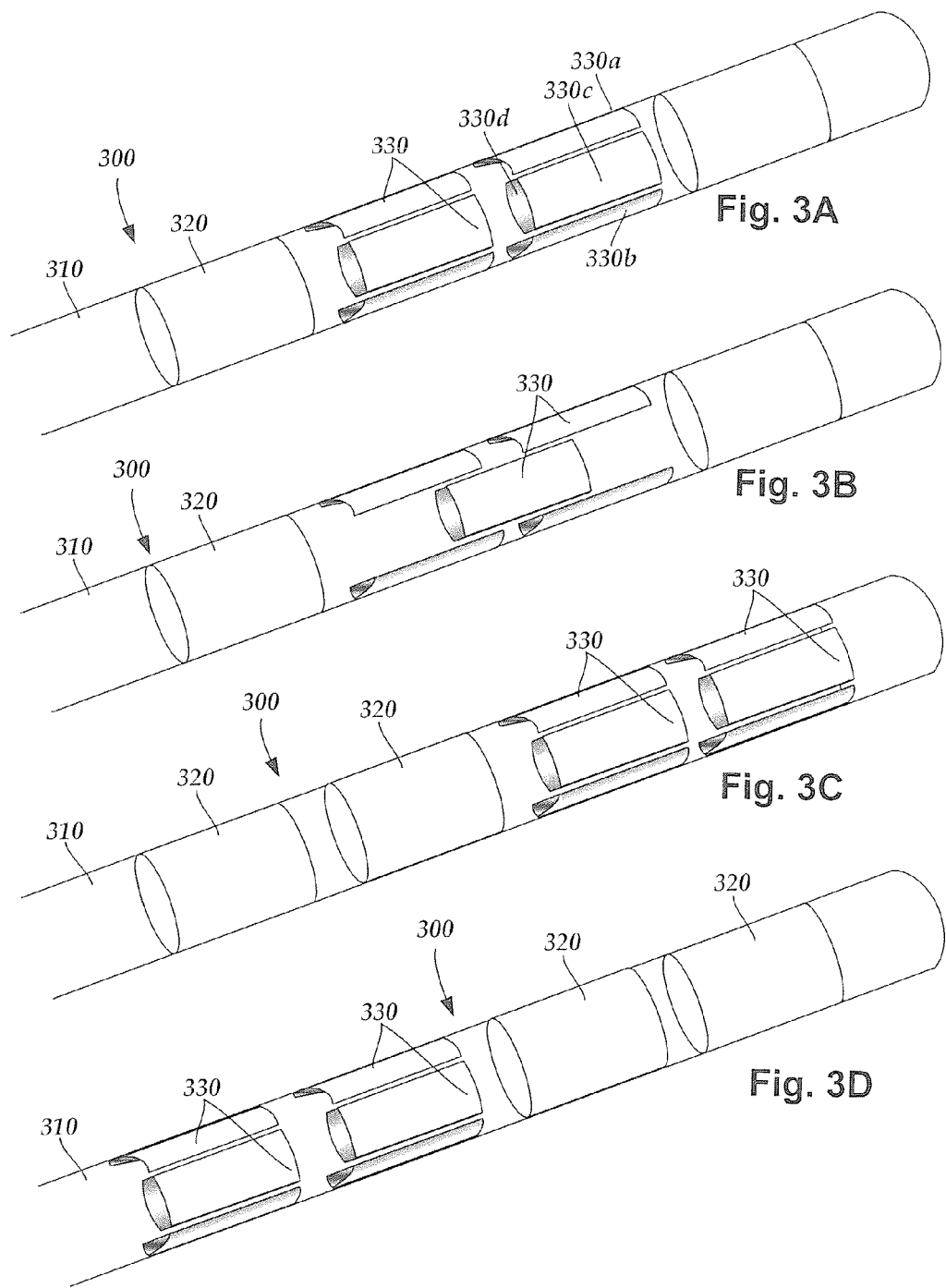

METHODS OF MAKING SEGMENTED ELECTRODE LEADS USING FLANGED CARRIER

CROSS-REFERENCE TO RELATED APPLICATIONS

This application claims the benefit under 35 U.S.C. §119 (e) of U.S. Provisional Patent Application Ser. No. 61/872,465, filed Aug. 30, 2013, which is incorporated herein by reference.

FIELD

The invention is directed to the area of electrical stimulation systems and leads and methods of making and using the systems and leads. The present invention is also directed to electrical stimulation leads with segmented electrodes and formed using a flanged carrier, as well as methods of making and using the leads and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a method of making a stimulation lead. The method includes providing a carrier with a body having a first surface, a distal end, and a proximal end. The carrier also includes flanges and each flange has a leg portion attached to the body and extending away from the first surface at a non-zero angle with respect to the first surface. The method further includes attaching segmented electrodes to the first surface of the body of the carrier; attaching conductors to the segmented electrodes; forming the carrier into a cylinder with the cylinder defining a central longitudinal axis through a center of the cylinder with the segmented electrodes disposed within the cylinder and the leg portions of the flanges extending toward the central longitudinal axis of the cylinder; molding a lead body around the segmented electrodes disposed on the carrier and around the flanges; and removing at least a portion of the carrier to separate the segmented electrodes.

Another embodiment is a method of making a stimulation lead. The method includes providing a carrier with a body having a first surface, a distal end, and a proximal end. The carrier also includes flanges with each flange having a leg portion attached to the body and extending away from the first surface at a non-zero angle with respect to the first surface. The flanges include a first flange extending from the distal end of the body and a second flange extending from the proximal end of the body. The method further includes attaching segmented electrodes to the first surface of the body of the carrier; attaching conductors to the segmented electrodes; forming the carrier into a cylinder with the cylinder defining a central longitudinal axis through a center of the cylinder with the segmented electrodes disposed within the cylinder and the leg portions of the flanges extending toward the central longitudinal axis of the cylinder; molding a lead body around the segmented electrodes disposed on the carrier and around the flanges; and removing at least a portion of the carrier and at least the first flange to separate the segmented electrodes.

Yet another embodiment is an arrangement including a carrier with a body having a first surface, a distal end, a proximal end, and flanges with each flange having a leg portion attached to the body and extending away from the first surface at a non-zero angle with respect to the first surface; and segmented electrodes attached to the first surface of the carrier.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a perspective view of an embodiment of a portion of a lead having a plurality of segmented electrodes, according to the invention;

FIG. 3B is a perspective view of a second embodiment of a portion of a lead having a plurality of segmented electrodes, according to the invention;

FIG. 3C is a perspective view of a third embodiment of a portion of a lead having a plurality of segmented electrodes, according to the invention;

FIG. 3D is a perspective view of a fourth embodiment of a portion of a lead having a plurality of segmented electrodes, according to the invention;

DETAILED DESCRIPTION

The invention is directed to the area of electrical stimulation systems and leads and methods of making and using the systems and leads. The present invention is also directed to electrical stimulation leads with segmented electrodes and formed using a flanged carrier, as well as methods of making and using the leads and electrical stimulation systems.

A lead for deep brain stimulation can include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and U.S. patent applications Ser. Nos. 12/177,823; 13/667,953; and 13/750,725, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead can include both recording electrodes and stimulation electrodes or electrodes can be used for both recording and stimulation.

Figure 1:
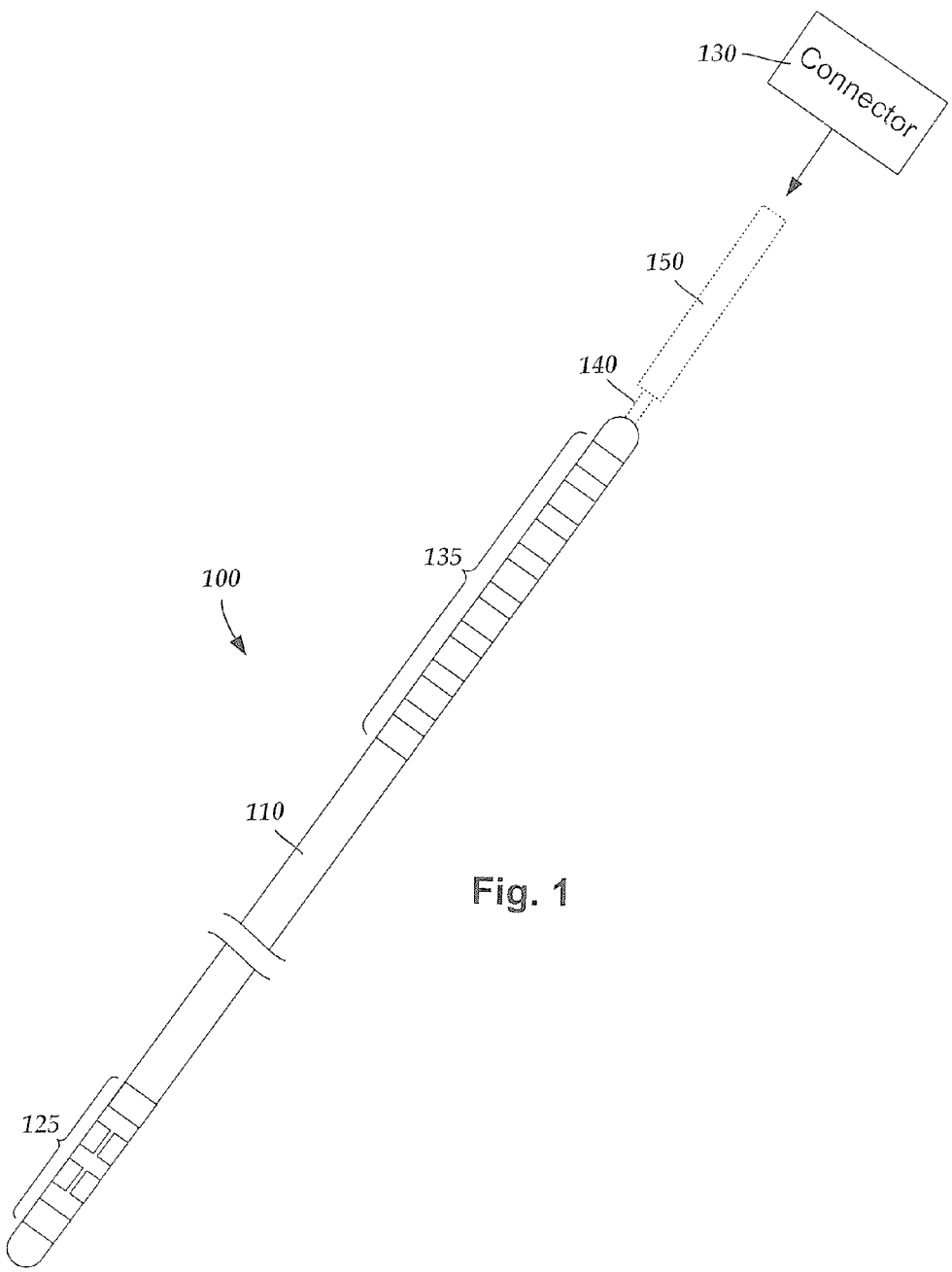
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator can have more or fewer than eight stimulation channels (e.g., 4-, 6-, 16-, 32-, or more stimulation channels). The control unit can have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more of the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (I. e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 can be disposed on any part of the lead body 110, usually near a distal end of the lead 100. In FIG. 1, the lead 100 includes two ring electrodes 120. Any number of ring electrodes 120 can be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes can be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see, e.g., tip electrode 320a of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

The lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

When the lead 100 includes both ring electrodes 120 and segmented electrodes 130, the ring electrodes 120 and the segmented electrodes 130 may be arranged in any suitable configuration. For example, when the lead 100 includes two ring electrodes 120 and two sets of segmented electrodes 130, the ring electrodes 120 can flank the two sets of segmented electrodes 130 (see e.g., FIGS. 1, 3A, and 3E-3H). Alternately, the two sets of ring electrodes 120 can be disposed proximal to the two sets of segmented electrodes 130 (see e.g., FIG. 3C), or the two sets of ring electrodes 120 can be disposed distal to the two sets of segmented electrodes 130 (see e.g., FIG. 3D). One of the ring electrodes can be a tip electrode (see, tip electrode 320a of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Figure 3E:
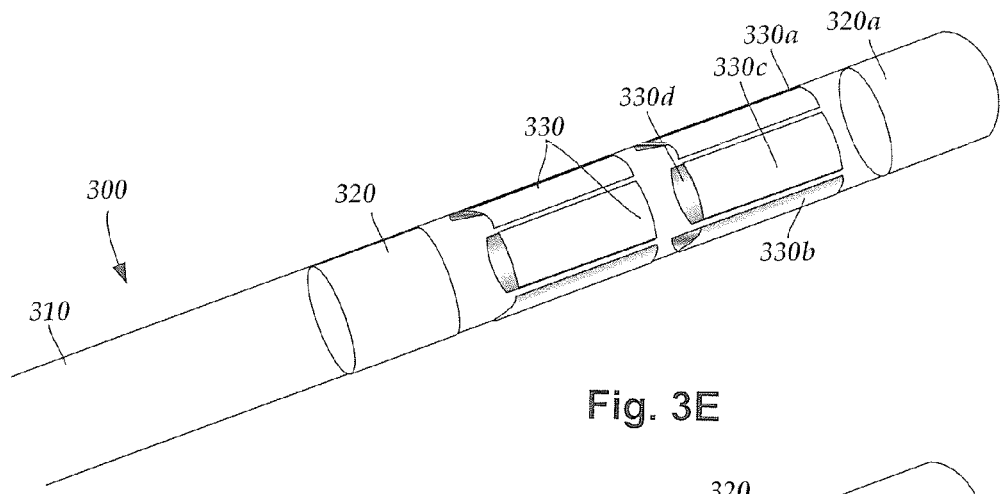
FIG. 3E is a perspective view of a fifth embodiment of a portion of a lead having a plurality of segmented electrodes, according to the invention.
Figure 3F:
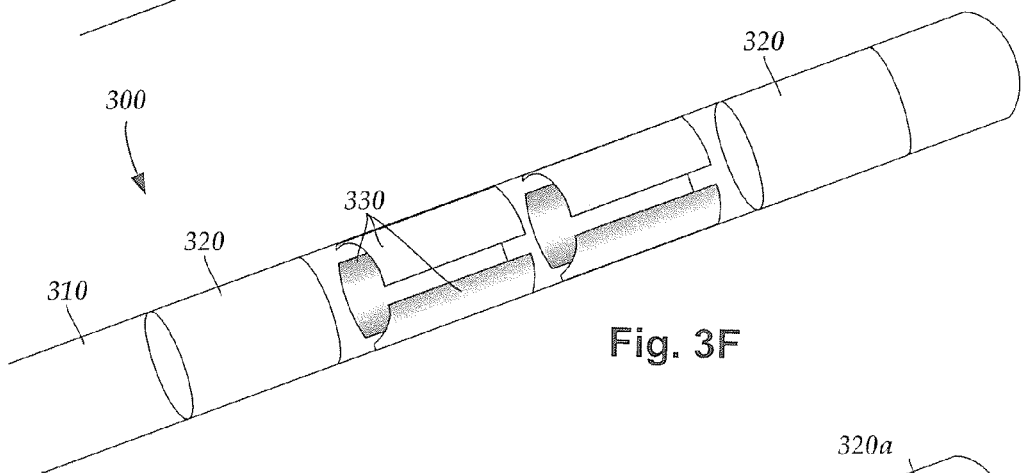
FIG. 3F is a perspective view of a sixth embodiment of a portion of a lead having a plurality of segmented electrodes, according to the invention.
Figure 3G:
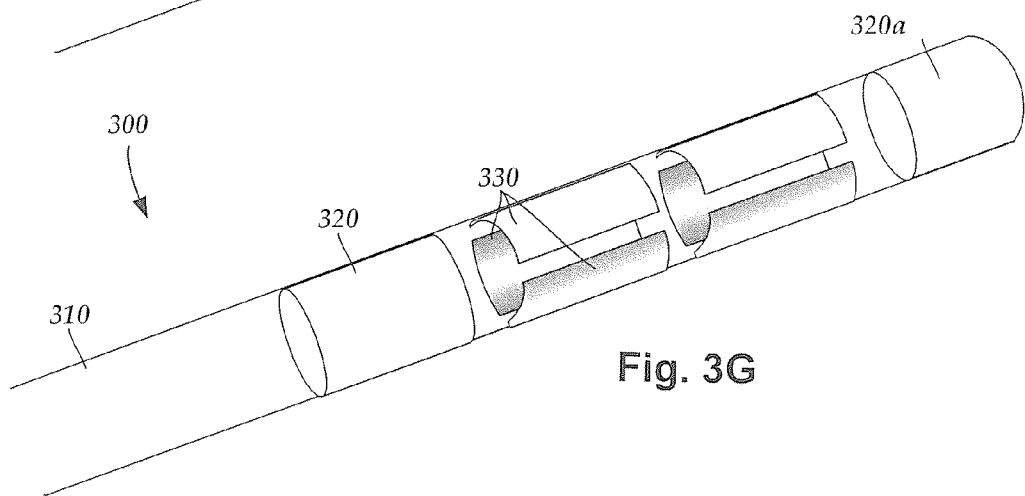
FIG. 3G is a perspective view of a seventh embodiment of a portion of a lead having a plurality of segmented electrodes, according to the invention.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration (FIGS. 3A and 3E). It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. The embodiments of FIGS. 3F, 3G, and 3H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F, 3G, and 3H has two sets of segmented electrodes, each set containing three electrodes disposed around the circumference of the lead, flanked by two ring electrodes (FIGS. 3F and 3H or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
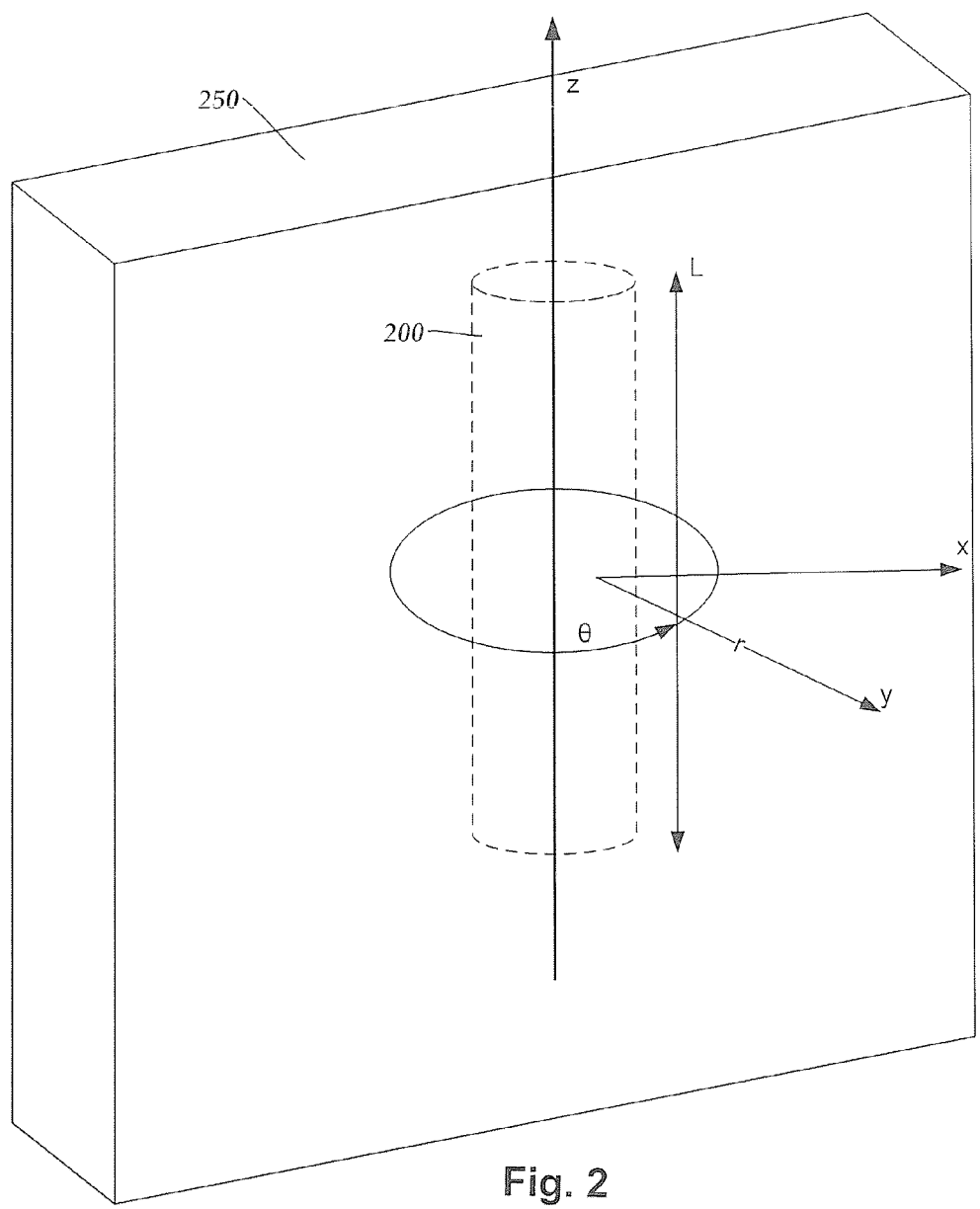
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

In other embodiments, individual electrodes in the two sets of segmented electrodes 130 are staggered (see, FIG. 3B) relative to one another along the length of the lead body 110. In some cases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

Figure 3H:
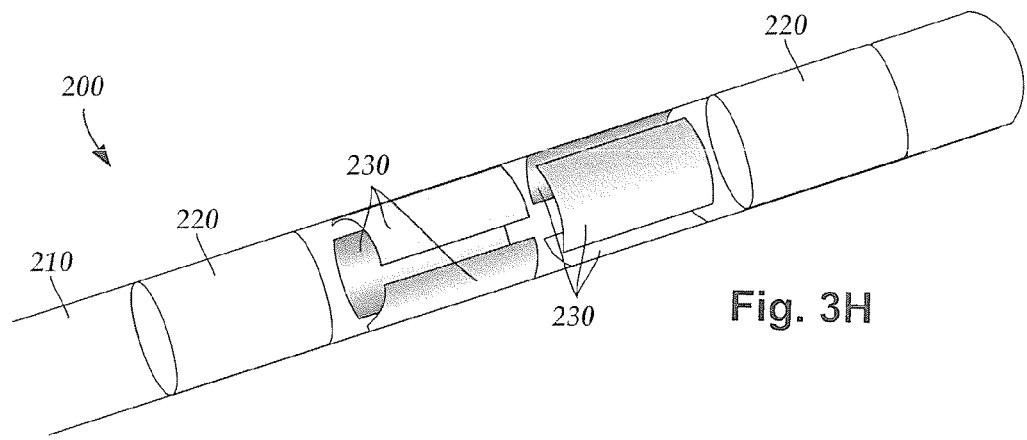
FIG. 3H is a perspective view of an eighth embodiment of a portion of a lead having a plurality of segmented electrodes, according to the invention.

FIGS. 3A-3H illustrate leads 300 with segmented electrodes 330, optional ring electrodes 320 or tip electrodes 320a, and a lead body 310. The sets of segmented electrodes 330 each include either two (FIG. 3B), three (FIGS. 3E-3H), or four (FIGS. 3A, 3C, and 3D) or any other number of segmented electrodes including, for example, three, five, six, or more. The sets of segmented electrodes 330 can be aligned with each other (FIGS. 3A-3G) or staggered (FIG. 3H)

Any other suitable arrangements of segmented electrodes can be used. As an example, arrangements in which segmented electrodes are arranged helically with respect to each other. One embodiment includes a double helix.

Figure 4A:
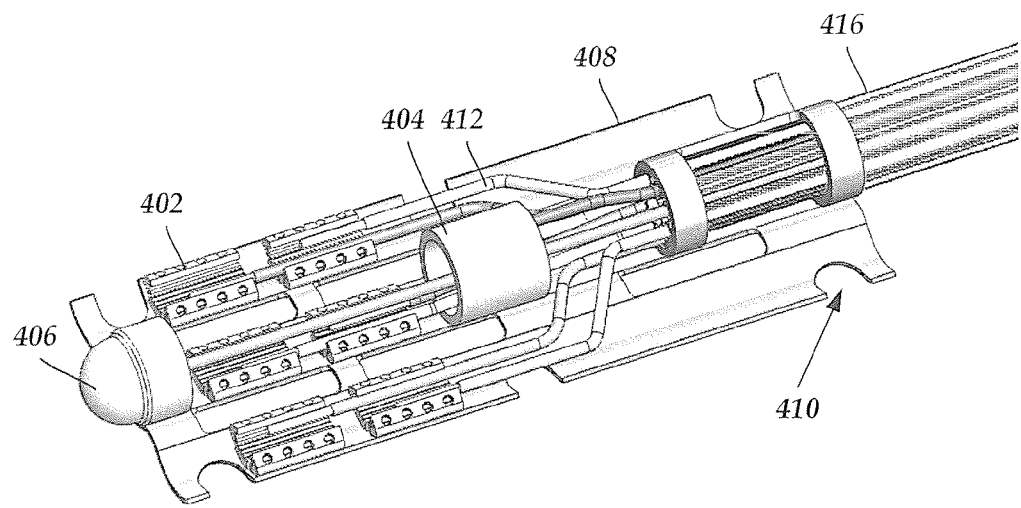
FIG. 4A is a schematic perspective view of one embodiment of an arrangement with electrodes disposed on a removable carrier, according to the invention.
Figure 4B:
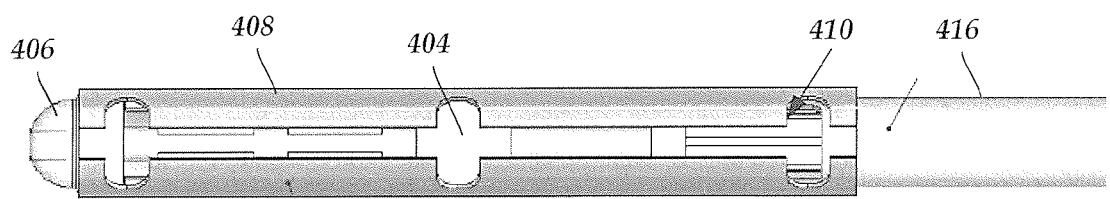
FIG. 4B is a schematic side view of the arrangement of FIG. 4A formed into a cylindrical construction, according, to the invention.

FIGS. 4A and 4B illustrate one embodiment of a method of making a lead with segmented electrodes. In this embodiment, multiple segmented electrodes 402, one or more optional ring electrodes 404, and an optional tip electrode 406 are attached to a carrier 408, as illustrated, for example, in FIG. 4A. The electrodes 402, 404, 406 can be attached to the carrier 408 using any suitable method including, but not limited to, welding, soldering, mounting using an adhesive (e.g., an epoxy), and the like. Preferably, the carrier material (and any supplemental material, such as a solder or adhesive used to attach the electrodes to the carrier) is biocompatible as small amounts of such materials may remain on the finished lead. It will be understood that selection of a carrier material may limit the method of attachment of the electrodes to the carrier or selection of the method of attachment may limit the carrier material that can be used.

As illustrated, multiple segmented electrodes 402 are attached to the carrier in an arrangement that, when the carrier is formed into a cylinder, result in the segmented electrodes being positioned in a desired arrangement (e.g., as one or more sets of segmented electrodes as illustrated, for example, in FIGS. 3A-3H) on the lead. The segmented electrodes 402 can be formed in any suitable shape or size and can be formed of the materials described above. In at least some embodiments, the segmented electrodes have a curved shape. The curved shape preferably corresponds to the curvature of the lead. For example, the curved shape of the segmented electrodes can have an arc of at least 10, 15, 20, 30, 40, 50, or 60 degrees. The arc of the segmented electrode may be no more than 345, 330, 320, 300, 270, 180, or 175 degrees. In some instance, the arc of the segmented electrodes is in the range of 10 to 345 degrees or in the range of 30 to 300 degrees or in the range of 50 to 180 degrees or in the range of 15 to 175 degrees.

Figure 5:
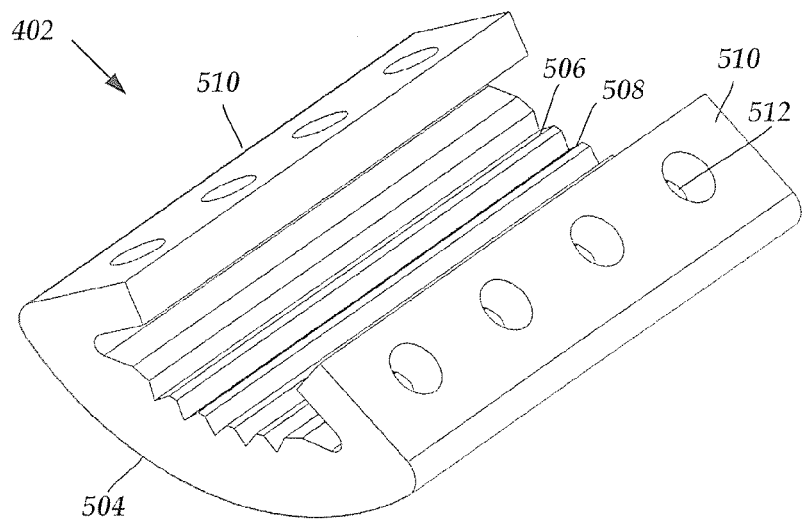
FIG. 5 is a schematic perspective view of one embodiment of a segmented electrode, according to the invention.

The segmented electrodes 402 optionally include one or more additional features to aid in holding the segmented electrode within the lead. One embodiment of a segmented electrode 402 displaying several optional features is provided in FIG. 5. The segmented electrode includes a stimulation surface 504 that, when the lead is formed and inserted into the patient, will be exposed to patient tissue. The segmented electrode also includes an interior surface 506 opposing the stimulation surface 504. The interior surface 506 will be in the interior the lead. One optional feature that aids in anchoring the segmented electrode 402 within the lead is a corrugated, or otherwise rough or non-uniform, texture 508 of the interior surface 506. The non-uniform texture 508 of the interior surface 506 increases the surface area that contacts the material of the lead body that is formed around the segmented electrode 402, as described below, and helps in retaining the segmented electrode within the lead. The corrugation of the texture 508 can have a triangular cross-section, as illustrated in FIG. 5, or any other suitable shape including, but not limited, a square, rectangular, trapezoidal, hemispherical, hexagonal, or any other regular or irregular cross-section. Other examples of suitable non-uniform textures include, but are not limited to, a checkerboard arrangement that is similar to corrugation but with intersecting grooves, an arrangement with multiple cleat-like projections or dimples extending from the surface 506, or a surface with a texture formed by knurling, grit blasting, or other methods of roughening of the surface, and the like.

Another optional feature of the segmented electrode 402 is one or more anchoring tabs 510. The anchoring tabs 510 are arranged so that they project into the interior of the lead and into the material of the lead body that is formed around the segmented electrode. The anchoring tabs can have any suitable size or shape and may optionally include one or more holes 512 in the tabs. In at least some embodiments, material from the lead body may flow into the holes 512 during the molding process to provide additional anchoring. When the segmented electrode 402 includes more than one anchoring tab 510, the anchoring tabs may be arranged around the segmented electrode in any suitable arrangement. For example, as illustrated in FIG. 5, two anchoring tabs 510 may extend from opposing sides towards each other. In other embodiments, the two anchoring tabs may extend from only a portion of a particular side of the segmented electrode 402. For example, two anchoring tabs may extend from the segmented electrode 402 with one tab extending near one end of a side of the electrode and the other tab extending near the other end of the opposing side of the electrode so that the two tabs are diagonally opposed. It will be understood that other arrangements can be used including, for example, arrangements in which tabs are directly opposed.

Returning to FIG. 4A, optionally one or more ring electrodes 404 and an optional tip electrode 406 may be included. These ring electrodes can be positioned at an end of the carrier 408, as illustrated in FIG. 4A, or between sets of segmented electrodes, or any combination thereof It will be recognized that some embodiments may not include ring electrodes or a tip electrode.

The carrier 408 is a structure to which the electrodes 402, 404, 406 are attached for manufacture of the lead. The carrier is typically relatively thin and can be made of any suitable material that is sufficiently flexible to be formed into a cylinder as described below. Such materials include, but are not limited to, metals (e.g., iron, aluminum, and the like), alloys (e.g., MP35N, steel, stainless steel, and the like), and plastics (e.g., plastic films such as those used for flexible circuits such as polyimide, polyetheretherketone (PEEK), polyetherimide, polyethylene naphthalate, polyethylene terephthalate, other polyesters, fluoropolymers, and the like). In at least some embodiments, the carrier may be flat or the carrier may be formed into one or more curved sections in anticipation of forming a cylinder, as described below. The carrier 408 may include one or more features, such as slots 410 to facilitate formation of the carrier into a cylinder, as described below. Such features may act, for example, as tooling aids or registration aids or a combination thereof.

Conductors 412 are attached to the electrodes 402, 404, 406. The conductors 412 can be, for example, insulated wires with a portion of the insulation removed to make contact with the electrodes 402, 404, 406. A different conductor 412 can be attached to each electrode 402, 404, 406, as illustrated in FIG. 4A. In other embodiments, the same conductor may be attached to two or more of the electrodes. The conductors 412 can be attached by any suitable method including, but not limited to, welding, soldering, crimping, using a conductive adhesive, and the like. The conductors 412 can be attached to any suitable part of the electrodes 402, 404, 406. For example, the conductors 412 can be attached to the interior surface or tabs of a segmented electrode 402 or the conductors 412 can be attached to an interior surface of the ring electrodes 404. As described above, the conductors 412 are typically attached to terminals (not shown) disposed at a proximal end of the lead. A portion of the conductors proximal to the electrodes may be disposed in a sleeve 416 that can be formed of a polymer material. In at least some embodiments, the sleeve may form part of the lead body. In at least some embodiments, the sleeve 416 defines a central lumen (not shown) and one or more outer lumens (not shown) that carry the conductors 412. Optionally, the central lumen may accommodate a stylet.

During manufacture, the carrier 408 is formed into a cylinder, as illustrated, for example, in FIG. 4B. In at least some embodiments, the carrier 406, with the electrodes 402, 404, 406 disposed thereon, is wrapped around a mandrel (not shown) to facilitate formation of the cylinder.

Once the carrier 408 is formed into a cylinder, a lead body is formed around the carrier 408 and electrodes 402, 404, 406. For example, the carrier 408 and the associated electrodes 402. 404, 406 are disposed in a mold and plastic material is introduced into the mold to form the lead body. Any suitable molding technique can be used including, but not limited to, injection molding (e.g., rotary injection molding) and compression molding. The plastic material of the lead body may cover all or a portion of the carrier 408 or, alternatively, may cover none of the carrier. Preferably, the material of the lead body is introduced beneath the carrier and is disposed around the electrodes 402, 404, 406 so that at least the interior surfaces of the electrodes 402, 404, 406 is in contact with the material of the lead body and the tabs, if any, extend into the material of the lead body.

Suitable materials for the lead body include biocompatible polymer materials, such as silicone, polyurethane, polyethylene, polyurea, polyurethane-urea, polyetheretherketone, and the like. The material introduced into the mold may be a polymer itself (for example, a polymer that has been heated to a fluid or semi-fluid state) or the material may be a pre-polymer material monomers or oligomers) that is polymerized during the molding process. After forming the lead body, the assembly can be removed from the mold. Although the process has been described using a single molding step, it will be recognized that multiple molding steps, using the same or different materials, can be utilized in forming the lead body.

After molding the lead body, the carrier 408 is removed leaving the electrodes 402, 404. 406 disposed in the lead body. The carrier 408 can be removed by any suitable method such as, for example, grinding (e.g., centerless grinding), etching, cutting, degrading an adhesive to release the carrier, laser ablation, and the like. Suitable methods for removal of the carrier 408 may depend on the materials of the carrier and other components of the lead (for example, the electrodes 402, 404; 406 and the lead body). In some embodiments, removal of the carrier 408 may also include removal of a small portion from the exposed surface of the electrodes 402, 404, 406 to facilitate complete or nearly complete removal of the carrier. Alternatively, a portion of the carrier may be left on one or more of the electrodes. Further description of embodiments of this method can be found in U.S. Patent Application Publication No. 2011/0078900, incorporated herein by reference.

One potential issue when manufacturing the lead as described above is that during removal of the carrier, or during other portions of the manufacturing process, the cylindrical arrangement may spring open. To address this issue, flanges can be provided on the carrier to hold the cylindrical arrangement in place after formation of the lead body.

Figure 6:
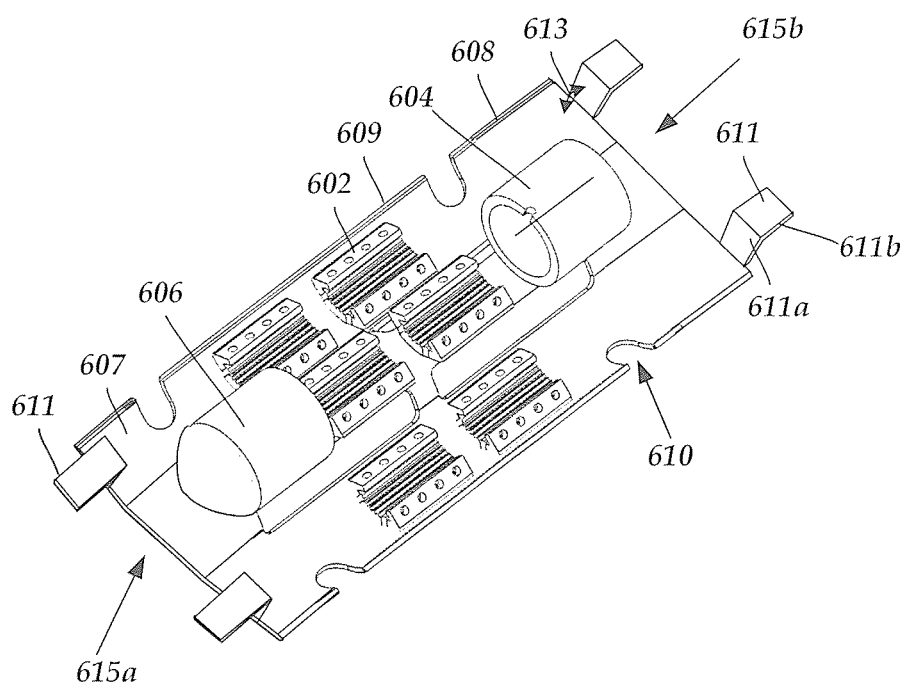
FIG. 6 is a schematic perspective view of one embodiment of an arrangement with electrodes disposed on a removable carrier having flanges, according to the invention.

FIG. 6 illustrates one embodiment of an arrangement for use in a method of making a lead with segmented electrodes. In this embodiment, multiple segmented electrodes 602, one or more optional ring electrodes 604, and an optional tip electrode 606 are attached to a surface 607 of a carrier 608. The carrier 608 has a body 609 and one or more flanges 611 that extend from the body of the carrier at a non-zero angle 613 with respect to the surface 607, as illustrated in FIG. 6. The carrier may also have slots 610. Unless otherwise indicated, the arrangement and design considerations for the segmented electrodes 602, ring electrodes 604, tip electrode 606, carrier 608 and slots 612 are the same as those for the similarly named elements described above with respect to FIGS. 4A, 4B, and 5. Moreover, although not illustrated in FIG. 6, a conductor is attached to each electrode 602, 604, 606, as described above with respect to FIGS. 4A and 4B, and a sleeve or other arrangement can be provided with the conductors as described above with respect to FIGS. 4A and 4B.

The flanges 611 can be provided anywhere along the body 609 of the carrier 608. In at least some embodiments. one, two, three, four, or more flanges 611 can be provided at a distal end 615a of the carrier 608. These flanges 611 may be distal to all of the electrodes 602, 604, 606 and, in particular, to the optional tip electrode 606, if present. In at least some embodiments, one, two, three, four or more flanges can be provided at a proximal end 615b of the carrier 608. In some embodiments, flanges 611 are provided at both the distal end 615a and proximal end 615b of the carrier 608, as illustrated in FIG. 6. It will be recognized, however, that flanges may be placed anywhere along the surface 607 of the body of the carrier as long as the flanges do not interfere with the electrodes and other components attached to the carrier. The flanges 611 may be integrally formed with the body 609 of the carrier 608 (e.g., stamped or cut out with the body and then bent into the desired arrangement) or can be attached to the body 609 using any suitable attachment method, including, but not limited to, welding, soldering, attaching with adhesive, and the like.

The flanges 611 are intended to be disposed within the lead body material, as described in more detail below. to reduce or prevent the likelihood of the carrier 608 opening up after it has been rolled into a cylinder and the lead body material has been molded around and within the carrier. Accordingly, any suitable flange structure that accomplishes this objective is contemplated. For example, in the illustrated embodiment, each flange 611 includes a leg portion 611a that extends from the body at the angle 613 with respect to surface 609. The flange 611 may also contain an optional foot portion 611b that is bent with respect to the leg portion 611a. The foot portion 611b may be bent away from the body 609 of the carrier 608 or may be bent toward the body of the carrier so long as the foot portion does not interfere with the electrodes and other components attached to the carrier. The angle 613 between the leg portion 611a and the surface 609 is non-zero with respect to the surface 609. In some embodiments, the angle 613 is in the range of 15 to 155 degrees or in the range of 30 to 150 degrees or in the range of 45 to 135 degrees or in the range of 60 to 120 degrees or in the range of 80 to 100 degrees or is in the range of 85 to 95 degrees or is 90 degrees.

Figure 7A:
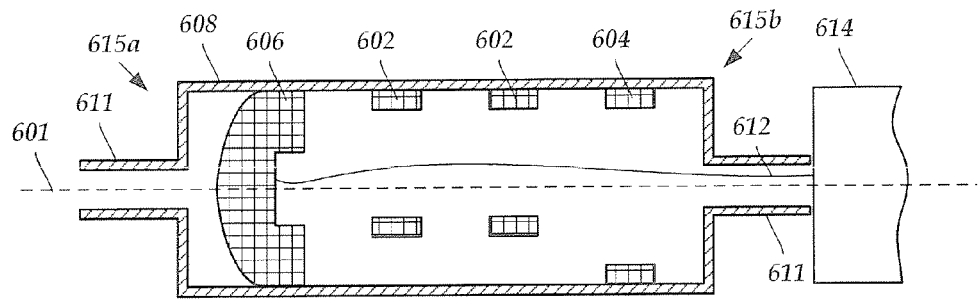
FIG. 7A is a schematic longitudinal cross-sectional view of the arrangement of FIG. 6 formed into a cylinder, according to the invention.
Figure 7B:
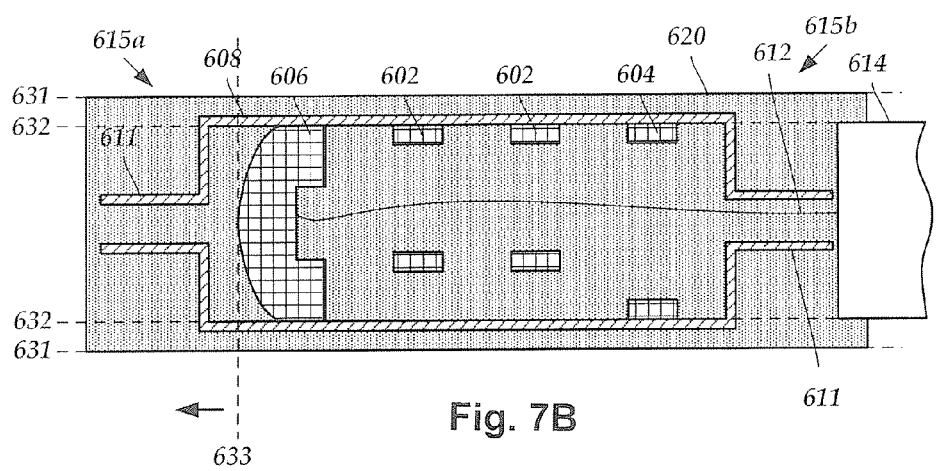
FIG. 7B is a schematic longitudinal cross-sectional view of the arrangement of FIG. 6 formed into a cylinder with lead body material disposed around the arrangement, according to the invention.
Figure 7C:
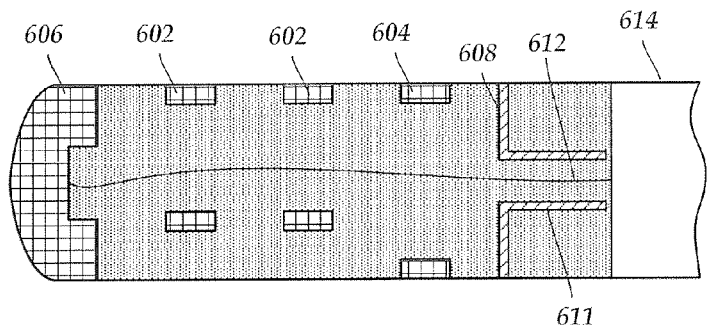
FIG. 7C is a schematic longitudinal cross-sectional view of the arrangement of FIG. 6 formed into a cylinder with the lead body material and a portion of the carrier trimmed away to expose the electrodes, according to the invention.
Figure 8:
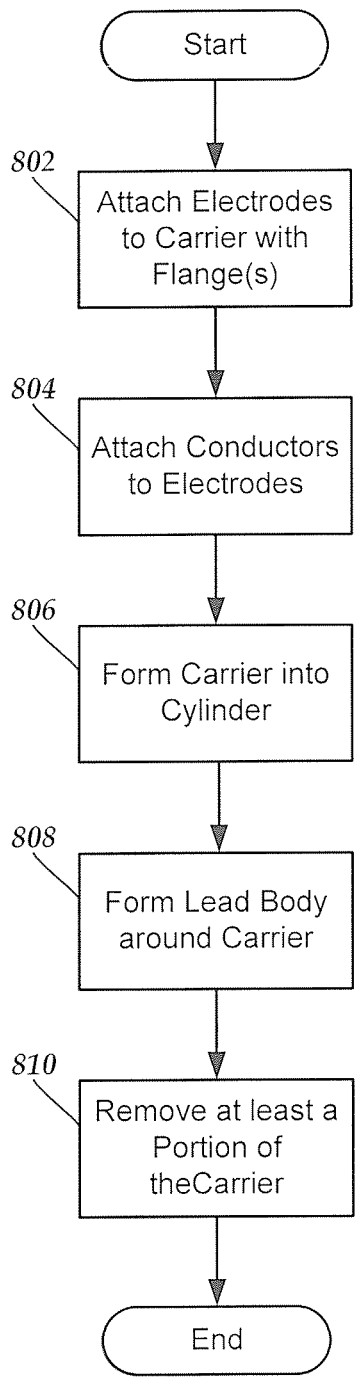
FIG. 8 is a schematic flowchart of one embodiment of a method of manufacturing a lead, according to the invention.

FIGS. 7A-7C illustrate, in cross-section, different stages in one embodiment of a method of manufacture of a lead using the arrangement illustrated in FIG. 6. In addition, FIG. 8 provides a. flowchart of one embodiment of a method of manufacture. Beginning at step 802 in FIG. 8, multiple electrodes 602, 604, 606 are attached to a carrier 608, as illustrated, for example, in FIG. 6. Conductors 612 (see, FIGS. 7A-7C and FIG. 4A) are attached to the electrodes 602, 604, 606 (step 804 of FIG. 8).

In step 806 (FIG. 8), the carrier 608 is formed into a cylinder, as illustrated, for example, in FIG. 7A. The arrangement of FIG. 6 may be formed into a cylinder around a mandrel (not shown) or any other suitable object or may be formed into a cylinder without a mandrel or the like. In the illustrated embodiment, at least some of the flanges 611 at the distal end 615a and at the proximal end 615b are disposed opposite each other when the cylinder is formed. The flanges 611 also extend from the body of the carrier 608 toward a longitudinal axis 601 defined by the cylindrical arrangement. For clarity of illustration, only one of the conductors 612 and the sleeve 614 is illustrated in FIGS. 7A-7C. It will be understood that other conductors (not shown) are also provided to couple to each of the electrodes 602, 604, 606. In at least some embodiments. the conductors enter the arrangement between the flanges 611 at the proximal end 615b of the carrier 608, as illustrated in FIGS. 7A-7C.

Once the carrier 608 is formed into a cylinder, a lead body 620 is formed around the carrier 608, electrodes 602, 604. 606, and flanges 611 (step 808 of FIG. 8) as illustrated in FIG. 7B. For example, the carrier 608 and the associated electrodes 602, 604. 606 can be disposed in a mold.

Plastic material is introduced into the mold to form the lead body 620. Any suitable molding technique can be used including, but not limited to, injection molding (e.g., rotary injection molding) and compression molding. The material of the lead body 620 may cover all or a portion of the carrier 608 or, alternatively, may cover only the flanges 611 of the carrier. Preferably, the material of the lead body is introduced beneath the carrier 608 and is disposed around the electrodes 602, 604, 606 so that at least the interior surfaces of the electrodes is in contact with the material of the lead body and the tabs, if any, extend into the material of the lead body.

Suitable materials for the lead body include non-conductive, biocompatible polymer materials, such as silicone, polyurethane, polyethylene, polyurea, polyurethane-urea, polyetheretherketone, and the like. The material introduced into the mold may be a polymer itself (for example, a polymer that has been heated to a fluid or semi-fluid state) or the material may be a pre-polymer material (e.g., monomers or oligomers) that is polymerized during the molding process. After forming the lead body, the assembly can be removed from the mold. Although the process has been described using a single molding step, it will be recognized that multiple molding steps, using the same or different materials, can be utilized in forming the lead body. The material of the lead body 620 disposed around the flanges 611 assist in maintaining the carrier 608 and associated electrodes 602, 604, 606 in the cylindrical arrangement.

Turning to step 810 (FIG. 8), at least a portion of the carrier 608 is removed leaving the electrodes 602, 604, 606 disposed in the lead body 620, as illustrated, for example, in FIG. 7C. The portion of the carrier 608 can be removed by any suitable method such as, for example, grinding (e.g., centerless grinding), etching, cutting, degrading an adhesive to release the carrier, laser ablation, scraping, and the like or any combination thereof. In some embodiments, the portion of the lead body 620 and carrier 608 between the lines 631, 632 on the top and bottom of FIG. 7B is removed. In addition, in some embodiments, the portion of the lead body 620 and carrier 608 distal to line 633 in FIG. 7B is also removed by cutting, grinding, or any other suitable method. This can also include removing (by trimming, cutting, grinding, or the like) the flanges 611 attached to the distal end 615a of the carrier 608. Moreover, additional portions of the lead body 620 around the tip electrode 606 may be removed (e.g., by trimming, cutting, grinding, scraping, or the like) to expose more of the tip electrode (see, FIG. 7C). In at least some embodiments, the flanges 611 on the proximal end of the carrier 608 may remain within the final lead construction, as illustrated in FIG. 7C.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making a stimulation lead, the method comprising:
   providing a carrier comprising a body having a first surface, a distal end, and a proximal end, the carrier further comprising a plurality of flanges, wherein each flange comprises a leg portion attached to the body and extending away from the first surface at a non-zero angle with respect to the first surface;
   attaching a plurality of segmented electrodes to the first surface of the body of the carrier;
   attaching a plurality of conductors to the plurality of segmented electrodes;
   forming the carrier into a cylinder, wherein the cylinder defines a central longitudinal axis through a center of the cylinder with the plurality of segmented electrodes disposed within the cylinder and the leg portions of the plurality of flanges extending toward the central longitudinal axis of the cylinder;
   molding a lead body around the plurality of segmented electrodes disposed on the carrier and around the plurality of flanges; and
   removing at least a portion of the carrier to separate the segmented electrodes.

2. The method of claim 1, wherein at least two of the plurality of flanges are attached to the distal end of the body of the carrier.

3. The method of claim 2, wherein removing at least a portion of the carrier comprises removing the at least two of the plurality of flanges attached to the distal end of the body of the carrier.

4. The method of claim 1, wherein at least two of the plurality of flanges are attached to the proximal end of the body of the carrier.

5. The method of claim 4, wherein forming the carrier into a cylinder comprises forming the carrier into the cylinder with the plurality of conductors passing between the at least two of the plurality of flanges attached to the proximal end of the body of the carrier.

6. The method of claim 4, wherein removing at least a portion of the carrier comprises removing the portion of the carrier leaving within the lead at least a portion of each of the at least two of the plurality of flanges attached to the proximal end of the body of the carrier.

7. The method of claim 1, further comprising attaching at least one ring electrode to the first surface of the body of the carrier.

8. The method of claim 1, further comprising attaching a tip electrode to the first surface of the body of the carrier.

9. The method of claim 8, wherein at least two of the plurality of flanges are attached to the distal end of the body of the carrier and positioned distal to the tip electrode.

10. The method of claim 9, wherein removing at least a portion of the carrier comprises removing the at least two of the plurality of flanges attached to the distal end of the body of the carrier to expose the tip electrode.

11. The method of claim 1 wherein removing at least a portion of the carrier comprises removing the body of the carrier.

12. The method of claim 1, wherein each of the flanges further comprises a foot portion that extends from the leg portion at a bent angle.

13. A method of making a stimulation lead, the method comprising:
    providing a carrier comprising a body having a first surface, a distal end, and a proximal end, the carrier further comprising a plurality of flanges, wherein each flange comprises a leg portion attached to the body and extending away from the first surface at a non-zero angle with respect to the first surface, wherein the plurality of flanges comprises a first flange extending from the distal end of the body and a second flange extending from the proximal end of the body;
    attaching a plurality of segmented electrodes to the first surface of the body of the carrier;
    attaching a plurality of conductors to the plurality of segmented electrodes;
    forming the carrier into a cylinder, wherein the cylinder defines a central longitudinal axis through a center of the cylinder with the plurality of segmented electrodes disposed within the cylinder and the leg portions of the plurality of flanges extending toward the central longitudinal axis of the cylinder;
    molding a lead body around the plurality of segmented electrodes disposed on the carrier and around the plurality of flanges; and
    removing at least a portion of the carrier and at least the first flange to separate the segmented electrodes.

14. The method of claim 13, wherein removing at least a portion of the carrier comprises removing the portion of the carrier leaving within the lead at least a portion of the second flange.

15. The method of claim 13, further comprising attaching a tip electrode to the first surface of the body of the carrier.

16. The method of claim 15, wherein the first flange is positioned distal to the tip electrode.

17. The method of claim 13, wherein each of the flanges further comprises a foot portion that extends from the leg portion at a bent angle.

18. An arrangement, comprising
    a carrier comprising a body having a first surface, a distal end, and a proximal end, the carrier further comprising a plurality of flanges, wherein each flange comprises a leg portion attached to the body and extending away from the first surface at a non-zero angle with respect to the first surface; and
    a plurality of segmented electrodes attached to the first surface of the carrier.

19. The arrangement of claim 18, wherein the plurality of flanges comprises a first flange extending :from the distal end of the body and a second flange extending from the proximal end of the body.

20. The arrangement of claim 18, further comprising at least one of a tip electrode or a ring electrode attached to the first surface of the carrier.

* * * * *